United States Patent
Kaminska et al.

[11] Patent Number: 6,139,856
[45] Date of Patent: Oct. 31, 2000

[54] COMPOSITION USEFUL FOR PROVIDING ONE-STEP SURGICAL PREPARATION AND DRAPE

[75] Inventors: Grazyna Kaminska, San Antonio; Nancy Girard, Boerne; Ming Fan; H. Ralph Rawls, both of San Antonio, all of Tex.

[73] Assignee: Biomedical Development Corp., San Antonio, Tex.

[21] Appl. No.: 08/988,729

[22] Filed: Dec. 11, 1997

[51] Int. Cl.$^7$ ................................................. A61K 31/00
[52] U.S. Cl. .................. 424/404; 424/78.02; 424/78.03; 424/78.05; 424/78.35; 424/405
[58] Field of Search .................................. 424/404, 405, 424/78.02, 78.03, 78.05, 78.35; 514/772.1

[56] References Cited

U.S. PATENT DOCUMENTS

| | | |
|---|---|---|
| 3,987,000 | 10/1976 | Gleichenhagn et al. ............ 260/31.2 R |
| 4,374,126 | 2/1983 | Cardarelli et al. ......................... 424/81 |
| 4,379,863 | 4/1983 | Snyder ..................................... 523/105 |
| 4,914,140 | 4/1990 | Saitoh et al. ............................. 523/111 |
| 5,041,287 | 8/1991 | Driggers et al. .................... 260/31.2 R |
| 5,547,662 | 8/1996 | Khan et al. ............................ 424/78.03 |

*Primary Examiner*—Jose' G. Dees
*Assistant Examiner*—Kathryne E. Shelborne
*Attorney, Agent, or Firm*—John Lezdey

[57] ABSTRACT

This invention relates to an improved polyvinylidene fluoride-based composition useful for forming a flexible, tack-free, nonflammable, substantially fluid resistant barrier film with substantially improved durability and skin-adhesion properties. The composition providing a long-lasting protective barrier film capable of disinfecting the skin surface of normally present microorganisms upon initial application, and said film imparting continuous and prolonged antimicrobial properties to the skin surface through sustained release of an encapsulated antimicrobial agent. The barrier film is further capable of remaining substantially adherent to the skin surface after prolonged exposure to biological fluids. A kit and methods of use for the composition are disclosed.

23 Claims, 1 Drawing Sheet

COMPOSITION USEFUL FOR PROVIDING ONE-STEP SURGICAL PREPARATION AND DRAPE

The government owns certain rights in the present invention pursuant to grant number 1R41 AR/AG44435-01 from the National Institutes of Health.

FIELD OF THE INVENTION

The present invention relates to an improved polyvinylidene fluoride-based film forming composition, and a one-step method of use providing a combination preoperative skin preparation and surgical incise drape. More specifically, the invention relates to an improved polyvinylidene fluoride-based composition useful in eliminating normally present microorganisms and imparting prolonged protection against microbial rebound growth on the skin surface. The invention further relates to preventing exposure of the skin surface to biological fluids, such as, blood, urine, and fecal waste.

BACKGROUND OF THE INVENTION

Surgical wound infections are an important cause of morbidity, mortality, and excess hospital costs. Surgical wound infections are the second most frequently found nosocomial infection overall, and among surgical patients, surgical site infections are the most common nosocomial infection site. Three factors contribute to the risk of developing a surgical wound infection: 1) the amount of and type of microbial contamination of the wound; 2) the condition of the wound at the end of the operation; and 3) host susceptibility, that is, the patient's intrinsic ability to deal with microbial contamination. In immuno-compromised patients, a greater tendency for infections caused by resident skin bacteria exists. Surgical site infections, which may, for the most part be benign in normal patients, may be fatal to the immuno-compromised. It is therefore a goal of the present invention to control resident skin bacteria at the site of an invasive surgical procedure.

Illustrating the gravity of the problem, the Centers for Disease Control and Prevention reported the number of sepsis cases tripled from 1979 to 1992 due to increased invasive procedures in older and immune-suppressed patients. In the U.S., every year roughly 500,000 people acquire sepsis and 175,000 die. One conservative estimate of the average cost of a surgical site infection, as determined on the basis of an average extra length of hospital stay of five days is $7,500. In addition to these direct costs, there are significant consequences such as lost productivity due to missed workdays, emotional trauma inflicted on patients and health provider as a result of the development of surgical site infections, patient dissatisfaction with the outcome of the operation, and the fear of malpractice on the part of the health care provider.

In order to reduce the risk of wound infection and maximize primary healing, a preoperative skin preparation seeks to create a clean operative field while minimizing damage to the skin. The preoperative skin preparation reduces the risk of postoperative wound infection by removing soil and transient microorganisms from the skin, by reducing the resident microbial count to subpathogenic amounts in a short period of time, and by inhibiting rapid rebound growth of microorganisms.

The surgical site preparation objectives (scrub, antimicrobial painting of skin and draping of the surgical site) are to remove dirt, skin oil and microbes from the skin while also providing a barrier against microbial migration into the incision. It is desired these objectives be achieved with the least amount of skin irritation. It is suggested that the agent used for scrubs and painting be a broad-spectrum antimicrobial, provide residual protection, and be nontoxic. An ideal antiseptic solution leaves a residue on the skin surface that continues to exert antimcrobial activity throughout the surgical period. This residual film should inhibit recolonization of the skin flora from environmental contact, from centripetal spread of microbes originating outside the field of prepared skin, and from the resident flora within the prepared field.

Many of the common surgical skin preparation protocols employ a topical application of an antimicrobial agent. Typically, topical application of antimicrobial agents is accomplished using, for example, lotions, ointments, and preoperative skin preps. The initial application of the antimicrobial agent, however, frequently does not impart the desired antimicrobial properties and requires continued application. During a surgical procedure the antimicrobial agent may also be removed by the action of blood, biological fluids and saline washes applied to the site. These two problems may lead to a rebound of the microorganism flora, and result in postoperative wound infection. It is therefore advantageous to have a one-step antimicrobial delivery system capable of maintaining an aseptic environment at the surgical site before and following the surgical procedure.

Other surgical skin preparation protocols employ a preopertive scrub, paint and drape procedure. The preoperative scrub is generally performed with antibacterial compounds such as povidone-iodine, chlorhexidine and hexachlorophene for varied periods of time (2–10 minute scrubs). The skin is then painted (or sprayed) with the antimicrobial. Povidone-iodine preparations are most widely used. 3M Corporation has developed a one-time skin preparatory solution, DURAPREP™ (U.S. Pat. No. 4,584,192), that is painted on and dries within 2 minutes. Although skin scrubs and painting demonstrate initial microbial inhibtion, none have proven efficacious for longer surgical time periods.

Adhesive-backed film incise drapes are often applied after conventional skin preparation, and surgical incisions are made through the drape. Adhesive drapes have proven to be effective in preventing resident flora from migrating into the wound as long as they are not peeled back from the wound edges or loosened by trapped fluids or air. The intrinsic benefits and antimicrobial effectiveness of the traditional adhesive-backed incise drape, however, are negated by its problems with creasing, wrinkling, and separation from the wound edge.

Eliminating the current practice of using separate antimicrobial preparations and adhesive incise drapes would cut down on the cost of materials, reduce prep time, and decrease the time needed for anesthesia. A combination antimicrobial preparation and incise drape that could be uniformly applied would benefit the patient by reducing the incidence of infection, thereby improving the chances of successful surgery and limiting prolonged post-operative hospital stay due to nosocomial surgical infection.

Polyvinylidene fluoride (hereinafter occasionally abbreviated as PVDF) is a mechanically tough thermoplastic that readily and stably polymerizes without low molecular weight contaminants or chemical stabilizers. PVDF is approved for use by the Food and Drug Administration for repeated contact with food and by the National Sanitation Foundation under Standard 61 for high purity water systems. KYNAR® brand PVDF homopolymers and copolymers (Elf Atochem ATO, Philadelphia, Pa.) are also in compliance with US Pharmacopeia Classification VI. Materials safety sheets (MSDS) provided with the KYNAR® products indicate 100% of the respective polymer compound to be present with no detectable impurities.

The present invention addresses the problems in the art with an improved PVDF-based film-forming composition and one-step method of use for a combination preoperative skin preparation and surgical incise drape. No one before the present inventors realized and demonstrated that PVDF-based coatings could provide an excellent combination preoperative skin preparation and surgical incise drape as provided herein.

DESCRIPTION OF THE PRIOR ART

Various compositions are known in the art for forming a barrier film when applied to the skin surface. It is known that film forming compositions are useful for providing the skin with protection against irritants, biological fluids and microorganisms, and for forming protective wound bandages, and gloves, A desired film forming composition should be easily applied to the skin surface, substantially fluid resistant, tack-free, sufficiently permeable to water vapor transmission, adherent, long-lasting and flame resistant. Another preferred feature is the barrier films ability to serve as a vehicle for delivery of an antimicrobial agent and medicament to the skin surface.

For example, U.S. Pat. No. 3,987,000 teaches a film forming polymer composition for providing a protective bandage when applied to a wound site by spraying from an aerosol container. The composition comprises one or more esters of acrylic or methacrylic acid with one or more straight-chain or branched monovalent, primary or secondary aliphatic alcohols having one to four carbon atoms; one or more maleic acid monalkyl esters with 1 to 12 carbon atoms in the alkly moiety; and isobutene. The composition is solubilized in a solvent, such as ethanol, acetone or methylene chloride. The solution is sprayed onto the skin surface using a liquefied propellant gas, such as a halogen hyrocarbon.

U.S. Pat. No. 4,374,126 teaches a composition and method of forming a film on a mammalian skin surface for providing long term protection against microorganisms. The composition comprises an alcohol soluble carboxylated polyacrylate including an antimicrobial agent, a topical adhesion promoter, and a difunctional amide for crosslinking the polymer upon evaporation of the alcohol solvent. The film is inert to body fluids, and provides prolonged antimicrobial properties to the skin by remaining adherent to the skin surface in excess of two days.

U.S. Pat. No. 4,379,863 teaches a copolymer-based composition for forming a breathable, water-insoluble barrier film providing the skin with protection from irritants, such as, urine or fecal waste. The copolymer comprises a solution of 50/50 n-buty/liso-butyl methacrylate, and a plasticizer dissolved in isopropanol. It is further taught that the barrier film is useful for providing protection at an interface between the skin surface and the adhesive of a prosthetic appliance.

U.S. Pat. No. 4,584,192 teaches a composition and method for forming a film containing complexed iodine as a broad spectrum antimicrobial for providing aseptic conditions on mammalian skin. The film-forming composition consist of monomers of an acrylic or methacrylic acid ester of an alkyl alcohol, and N-vinyl lactam. The composition is dissolved in an alcohol, such as, ethanol and isopropanol.

U.S. Pat. No. 4,914,140 teaches a composition for forming a protective barrier film on the skin that is less irritative because it contains no surfactants. The film is comprised of an acrylic copolymer of ethyl acrylate and methacrylate acid, and a cellulose derivative dissolved in an alcohol and water solvent mixture.

U.S. Pat. No. 5,547,662 teaches a composition for preparing a skin surface as a surgical site and includes the film forming material and an antimicrobial agent. The preferred embodiment of the invention consisting of a dye color change reactive to the elimination of the fugitive solvent. The said color change indicating the site is ready. The invention also teaches a use of the invention and a kit for its use.

U.S. Pat. No. 5,041,287 teaches a composition for forming a tough, flexible film providing spray-on bandages for mammalian skin surfaces, as well as, spray-on gloves and coatings for medical parts and/or electonic devices. The composition comprises polyvinylidene diflouride, an aqueous emulsion of acrylates and methacrylates, an unsaturated carboxylic acid and/or acrylamide, and a plasticizer dissolved in a fugitive solvent. The composition is applied to the skin and forms a film upon evaporation of the solvent. The composition forms a coating suitable for providing a non-notching polymeric coating which is readily removable and does not adhere to a wound area.

The inventors of the present invention sought to improve upon the composition of U.S. Pat. No. 5,041,287 in order to achieve a composition that formed a film with substantially greater toughness, adhesion, and durability in a humid environment. A film-forming composition usefull as an effective one-step preoperative skin preparation and surgical incise drape must embody a large number of characteristics. It must be substantially adherent to the skin surface in the presence of biological fluids, and be substantially resistant to degradation upon exposure to skin secretions and body oils. The composition must rapidly dry upon application to the skin surface providing a tough, flexible, thin long-lasting film. After forming, the film must adapt well to all skin movements, and be free of wrinkling, tearing, lifting or bubbling. The film must have a substantial moisture vapor transmission rate preventing interference with normal skin respiratory processes. Further, the film must be highly resistant to burning when exposed to the high energy lasers frequently employed in modem surgical suites for performing an incision. The application of the film composition should also be convenient, cost-effective, and capable of providing a film with sufficient microporosity for both maintaining the skins respiratory processes and supporting the release of an encapsulated antimicrobial agent.

The present inventors have actively investigated for a composition that satisfies the above requirements for use as a combination preoperative skin preparation and surgical incise drape. Satisfying the many above stated requirements, the inventors disclose a materially improved PVDF-based composition comprising an amine-substituted acrylic polymer component. The composition of the present invention provides a film with substantially enhanced durability and skin-adhesion promoting characteristics over the prior art. The present invention represents an unforeseen improvement over U.S. Pat. No. 5,041,287, and these improvements provide a film forming composition suitable for use as a combination surgical preparation and drape.

SUMMARY OF THE INVENTION

In accordance with one embodiment of the invention, an improved PVDF-based composition comprising an amine-substituted acrylic polymer component is provided that forms a barrier film with substantial improvements in skin-adhesion, toughness and durability over the prior art. The improved durability and skin-adhesion characteristics providing a longer lasting film for imparting prolonged delivery of an encapsulated antimicrobial agent to the skin surface.

The durability of the film is further illustrated by its resistance to physical removal.

The present invention provides an advantageous one-step method for eliminating surgical site microbial growth, and forming a surgical incise drape. The surgical incise drape rendering the interface between the skin and the film an aseptic environment before, during and following the surgical operation. In general the method involves applying the film forming composition to the surgical incision site, allowing the solvent to evaporate to form a thin, durable, substantially adherent film free of wrinkles and bubbles. The surgical incise drape being highly resistant to degradation and removal by biological fluids. The surgical incise drape being sufficiently microporous to sustain the release of an encapsulated antimicrobial agent while not interfering with the skin surfaces necessary respiratory processes. Further, the surgical drape is highly nonflammable.

Another embodiment of the invention is a method of use providing a protective barrier film on the skin surfaces of incontinent patients. The barrier film providing protection to the patients skin surface from body excretions, such as, urine, fecal matter and perspiration. The present invention being substantially resistant to degradation by said body excretions. The microporosity of the protective barrier film prevents interference with the skins respiratory processes, thus, allowing the application of large skin surface areas.

A preferred film forming composition comprising:

(a) about 30 to 60% by weight of solids selected from the group consisting of polyvinylidene diflouride and the copolymers thereof;

(b) about 10 to 20% by weight of solids of a polymer of monomers selected from the group consisting of an alkylacrylate, an alkyl (meth)acrylate, and the copolymers thereof;

(c) about 30 to 60% by weight of solids of a polymer of monomers selected from the group consisting of a dialkylaminoalkyl (meth)acrylate and the active salts thereof, and a lower alkyl (meth)acrylate;

(d) about 0.5 to 2.0% of water based on total composition weight;

(e) an effective amount of an antimicrobial agent; and (e) an aqueous organic solvent for dissolving all components;

wherein, said composition when applied to a skin surface from said solvent dries in less than one minute forming a substantially durable, substantially fluid resistant, tack-free barrier film substantially adherent to said skin surface, said barrier film capable of releasing said antimicrobial agent in an amount effective to substantially impart prolonged antimicrobial properties on said skin surface.

DETAILED DESCRIPTION OF THE INVENTION

Figure 1:
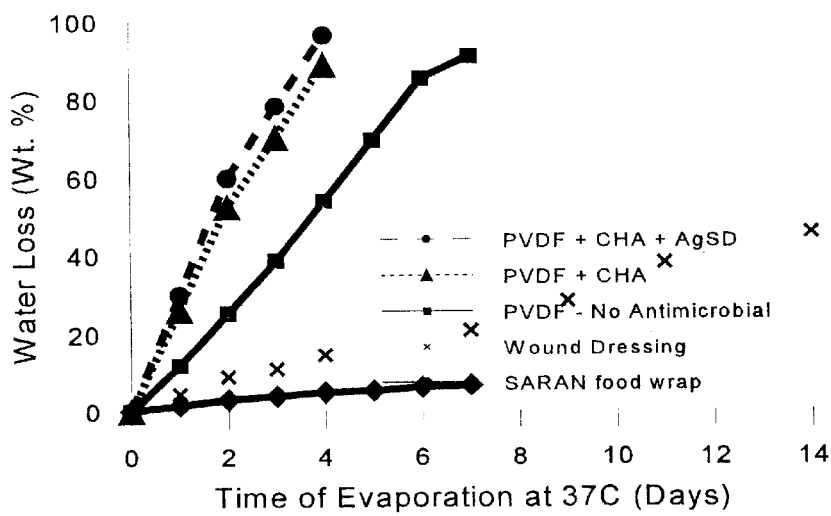
FIG. 1 illustrates the moisture vapor transmission rate (MTVR) for the present invention. The MTVR of the present invention containing both chlorhexidine acetate (CHA) and silver sulfadiazine (AgSD), chlorhexidine alone, and with no antimicrobial agent present is compared against BLISTERFILM™ hydrocolloid wound dressing and SARAN® food wrap. The percent of water loss is plotted versus time in days. The data illustrate the present invention is breathable, thereby providing patient comfort and promotion of wound healing. See Test #3 for details.

A problem addressed and resolved by the present invention is reducing the number of surgical wound associated infections with an improved PVDF-based composition comprising an admixture of PVDF, acrylic polymers, and an amine-substituted acrylic polymer. The composition of the present invention resulting in unforeseen improvements over the prior art (U.S. Pat. No. 5,041,287). The improvements including substantial increases in the PVDF-based films resistance to biological fluids, durability, and skin-adhesion properties. The improvements over the prior art forming a film having the desired features necessary for providing an effective one-step, preoperative skin preparation and surgical incise drape with sustained release of an antimicrobial agent. The antimicrobial agent eliminates microbes present on the skin surface and continues to inhibit any rapid rebound microbial growth over an extended period. The improved composition is soluble in a solvent, and when applied to the surgical incision site dries in less than a minute to form a substantially nonflammable surgical drape. Further, the improved composition does not cause primary irritancy and allergic sensitivity when contacted with skin.

The film forming composition of the invention is further suitable for use as a protective barrier on incontinent patients. The substantial skin-adhesion and durability of the invention achieves long-lasting protection against biological fluids, such as, urine, fecal matter, and resistance to detachment from the skin by body oils, perspiration and hot water. The coating has further applicability as both a protective barrier and a delivery system for preventing infection at the site of a dialysis artero-venous shunt, feeding tube, colostomy conduit, urinary catheter or the like.

A preferred embodiment of the invention is a barrier film with sufficient moisture vapor permeability supporting reduction of excessive moisture buildup that could macerate the skin and loosen the adhesion of the film. Another feature of the invention is a coating suitable for maintaining the isothermic environment appropriate for an individual's body temperature. To sustain both the desired isothermic environment and moisture vapor permeability, it is preferred the microporosity provide a moisture vapor transmission rate of 0.1 to 1.0 $g/cm^2/day$. The preferred composition forming a film with a suitable microporosity includes water. Use of an aqueous acrylic emulsion, such as Rhoplex B-15J, is an advantageous method for preparing a composition having the desired microporosity. Rhoplex B-15J, is an acrylic polymer available from Rohm & Hass, Philadelphia, Pa.

It is another feature of the invention that the microporosity characteristic enhances diffusion to the skin surface of the antimicrobial agent or medicament encapsulated within the barrier film. Typical antimicrobial agents deliverable to the skin surface from the film include antibiotics, iodophors, silver sulfadiazine, chlorhexadine and biologically active salts thereof. An effective antibiotic for preventing antimicrobial growth is nystatin utilized in the concentration ranging from about 0.5 to 2.0% of the total weight of said film forming composition. A more preferrable antibiotic is chlorhexidine acetate, or a chlorhexidine acetate and silver sulfadiazine combination with each at an effective concentration in the range of about 0.5 to 2.0%. The preferred composition comprising chlorhexidine and silver sulfadiazine provides a film having the desired microbicidal activity without altering film integrity or the desired microporosity.

The improved skin-adhesion property allows the film to remain attached to the skin for an extended time period allowing the prolonged delivery of a preferred antimicrobial agent.

A suitable medicament for delivery the skin surface includes an anti-inflammatory agent, a steroid, an antiviral agent, an antifungal, an anticoagulant, an antiphlogisitic, a chemotherapeutic, a hemostatic, a cytostatic, and a hormone.

A preferred embodiment of the composition further includes a dye soluble in the organic solvent for visually ascertaining the location of the skin surface coated with the composition. The dye can act as a visual indicator during the course of a surgical operation, or provide a means for determining when a new coating may be required. Suitable dyes having virtually no effect upon the characteristics of the film include the Drug and Cosmetic class of dyes, such as, Drug and Cosmetic Green No. 6. The preferred range of dye concentration is between 0.01% and 0.1% (w/w).

The preferred solvent provides a drying time of less than one minute, and compromises neither film toughness, resistance to detachment in a wet/humid environment, nor the microporous film morphology. Exemplary solvents providing the above stated requirements include acetone, ethyl acetate and mixtures thereof. The most preferrable of the solvents is acetone because of its excellent disinfectant qualities and its volatility provides a preferrable drying time of less than one minute.

Another preferred embodiment of the invention is the advantageous inclusion of a lipid component in the composition. The lipid component provides protection from irritation of the skin surface caused by the defatting action of the solvent. Suitable lipids are unsaturated fatty acids, saturated fatty acids, and sphingolipids. The most preferable of the lipids include ceramide Type III, ceramide Type IV, cholesterol, and linoleic acid. The preferred range of lipid concentration is between 0.25 and 2.0 parts by weight per 10,000 parts by weight of polymer solids.

It is a preferred feature of the invention that the surgical incision drape formed by the composition be nonflammable. Most modem surgical suites employ high energy devices to perform an incision at the surgical site. It is highly desirable that the film be substantially resistant to burning and charring when exposed to common high energy surgical devices.

The present invention provides a coating that is free of dermal irritation upon contact with the skin surface. It is a further feature of the invention that the improved composition does not elicit skin sensitization or delayed contact hypersensitivity.

Preferably the composition is composed of a solids content of about 5 to 10% by weight, providing suitable films with a thickness of about 0.010 mm to 0.015 mm when applied in single coatings to the skin surface. Films of varied thickness can be obtained using different methods of application that include painting, spreading, swapping, dipping or spraying. Alternatively, the thickness of the coating may be increased using multiple applications.

The preferred composition of the invention utilizes polyvinylidene diflouride homopolymer or a copolymer thereof. Suitable copolymers include tetrafluoroethane and hexafluoropropylene. The greater the PVDF concentration, the tougher the coating and ease with which it separates from the skin. For applications requiring flexibility, skin-adhesion and durability in a humid environment, it is preferrable to dilute the PVDF component by altering the copolymer content or by combination with an acrylic, such as, alkyl (meth)acrylate. For the present invention, other halogen based polyvinylidene homopolymers, such as polyvinylidene chloride (PVC) may also be utilized. For purposes of the present invention, a suitable range of PVDF is determined to be about 30 to 60% by weight of solids.

The composition of the invention comprises about 10 to 20% by weight of solids of a polymer of acrylic monomers selected from the group comprising alkyl (meth)acrylates. It is known that typical alkyl (meth)acrylates suitable for use in the invention comprise methyl acrylate, ethyl acrylate, butyl acrylate, methyl methacrylate, propyl methacrylate, ethoxyethyl acrylate, methoxyethyl acrylate, methoxyethyl methacrylate, ethoxyethyl methacrylate, and the like.

To prepare the composition of the invention it is beneficial to prepare an aqueous emulsion of the acrylic compounds prior to combining with the polyvinylidene fluouride. Preferred acrylic polymer dispersants include the following:

1. methyl methacrylate, butyl acrylate and acrylic acid
2. propyl methacrylate, butyl acrylate and acrylic acid
3. methoxyethyl methacrylate, butyl acrylate and acrylic acid
4. methyl methacrylate, 2-ethylhexyl acrylate and methacrylic acid.

The film forming composition of the present invention represents an unforeseen improvement over the prior art in it could not be foreseen that the addition of an amine-substituted acrylic polymer of monomers selected from a group consisting of dialkylaminoalkyl (meth)acrylate, and a lower alkyl (meth)acrylate would provide a composition forming a protective coating with substantial increases in skin-adhesion and durability in a humid environment. A preferred coating for forming a surgical drape comprises about 30 to 60% by weight of the amine-substituted acrylic polymer.

The inclusion of an amine-substituted acrylic polymer into the composition of the prior art provides a film capable of remaining substantially intact and 100% attached to a glass slide during 14 to 19 days of submersion in 37° C. water (Formulation in EXAMPLE 1). This represents a substantial increase in skin-adhesion and durability over the prior art (U.S. Pat. No. 5,041,287). Which appears to be capable of remaining intact and 100% attached to a glass slide for 24 to 48 hours of submersion in 37° C. water. When tested on human skin, the film of the present invention remained intact and 100% attached for at least 34 hours, while the film prepared from the prior art composition began to show separation at 20 hours. The preferred embodiment of skin-adhesion allows for greater retention of the film during a surgical procedure, providing the means for release of an encapsulated antimicrobial agent and protection of the surgical site from contamination.

Suitable dialkylaminoalkyl (meth)acrylates which can be used to prepare the amine-substituted acrylic polymer include N,N-dimethylaminoethyl (meth)acrylate, N,N-diethylaminoethyl (meth)acrylate, t-butylaminoethyl (meth) acrylate and active salts thereof. About 20 to 30% by weight the amine-substituted acrylic polymer to total solids content has been found suitable for the coatings of the present invention.

Suitable lower alkyl (meth)acrylates which can be used to prepare the amine-substituted acrylic polymer comprise those having 1 to 8 carbon atoms in the alkyl group such as methyl acrylate, ethyl acrylate, isopropyl acrylate, methyl methacrylate, propyl methacrylate, ethoxyethyl methacrylate, and the like.

A preferred composition for forming a surgical drape has a solids content of about 5 to 10%, and comprises about 30 to 60% by weight of polyvinylidene difluoride, 10 to 20% by weight of a mixture of methyl acrylate, and methyl methacrylate, and 30 to 60% by weight of a polymer comprising N,N-dimethylaminoethyl methacrylate, and methyl methacrylate.

It is a feature of the invention that the improved composition be used as a one-step method for a combination surgical site preparation and drape. The present invention can be applied by either painting, spreading, or spraying. After the composition is applied to the selected surgical site, the solvent is allowed to evaporate. The time allowed for evaporation is rapid, occurring in less than one minute. The presence of the dye in the composition provides the individual applying the film with the means to visualize whether the surgical site is adequately covered. Once the desired surgical site is covered, the film provides a substantially durable surgical incise drape that promotes aseptic conditions on the skin surface through the combined action of the solvent and sustained release of an encapsulated antimcrobial agent. The surgical incision can next be made through the surgical drape without burning or charring the film.

In practice, another feature of the invention is a kit for applying the composition to the skin surface including a sealed container having an application means. Preferably the application means is coupled to the container and comprises a pump spray, sponge, cloth, gauze, cotton, wool, brush, or roller ball applicator. A preferred feature of the kit is it can be contained within a sealed package that is capable of being sterilized, thus, providing a suitable and convenient means for applying the composition in the sterile environment of a surgical suite.

The following example compositions are provided to illustrate the invention, but are not to be considered to limit the invention. By way of example, a list of useful components and their sources is provided in Table I.

TABLE I

Commercially available sources of Components

| Ingredient | Product Identification | Source |
| --- | --- | --- |
| Vinylidene Fluouride - Tetra Fluoroethylene Copolymer | Kynar 7201 | Elf Atochem ATO Philadelphia, PA |
| Acrylic Copolymer | Rhoplex B-15J emulsion | Rohm and Haas Company Philadelphia, PA |
| Butylmethacrylate,2-Dimethylamino-ethyl Methacrylate, and Methyl Methacrylate Acrylic Copolymer | ®Eudragit E100 | Hüls America, Inc. Somerset, NJ |
| Acetone | dimethylketone: 2-propanone | Mallinckrodt Baker Inc. Paris, KY |

EXAMPLE 1

A composition suitable for forming a surgical incise drape was prepared as follows utilizing commercially available compositions.

| Component | Weight |
| --- | --- |
| Kynar 7201 | 5 g. |
| Rhoplex BJ-15 | 2.5 g. |
| Eudragit E 100 | 2.5 g. |
| Acetone | 90 g. |

The preparation of the composition is performed at room temperature with an anchor stirrer. The listed components are sequentially placed into a beaker, and the composition thoroughly mixed by stirring overnight to prepare a 10% by weight of polymer solids composition. The prepared composition readily forms a substantially adherent, durable film upon application to the skin surface and evaporation of the solvent.

EXAMPLE 2

Following the procedure of EXAMPLE 1, a film forming composition with the desired microbicidal activity was prepared comprising by weight both 0.5% chlorhexidine acetate and 0.5% silver sulfadiazine. 0.5 grams of each antimicrobial agent provides a PVDF-based coating suitable for eliminating normally present microbes from the surgical incision site, and preventing rapid rebound microbial growth. This composition providing a preferred one-step combination surgical site preparation and drape.

EXAMPLE 3

Following the procedure of EXAMPLE 1, a composition containing Cholesterol, Palmitic acid, Ceramide III and Ceramide IV was prepared. The resulting film provides a surgical incision drape that wards off the defatting action of the solvent in the composition. The quantities of the lipid in this example are provided in TABLE II.

TABLE II

| Lipid | mg of lipid/100 g of composition |
| --- | --- |
| Cholesterol | 0.4 mg |
| Palmitic acid | 0.09 mg |
| Ceramide III | 0.03 mg |
| Ceramide IV | 0.03 mg |

The invention is further illustrated by the following testing objectives.

TEST #1—FLAME PROPAGATION TEST

The tendency of the dried film of the invention to propagate a flame was determined using a modification of Underwriters Laboratory standard test UL94 "plastics materials for parts in devices and appliances" (1991).

Using the composition described in Example 1, a 75×25×1 mm glass microsope slide is coated by wiping with a composition flooded sponge. Either immediately, or after fully drying, the coated slide is passed through a Bunsen Burner flame to ignite the composition. The coated slide is inserted into the flame at varying angles to observe the extent to which a flame consumes the composition. In the 180° flame-propagation test, at 0°, the specimen points upward ("North") and a flame is carried away from the film. Thus, at 0° the coating is subjected to the mildest condition in the test. Highly flammable materials will support a flame at 0°. Slightly flammable materials will support a flame at 180°, but inflammable materials will not. At progressively decreasing intermediate angles (135°, 90°, 45°), less of the specimen is contacted by the flame; so the severity of the test is reduced as the angle is decreased. Therefore, the smaller the angle which supports the propagation of a flame, the greater the hazard.

Another aspect of fire hazard is the time during which initially flammable materials, such as solvent-based coatings, remain flammable after they are applied. This was evaluated by allowing the coatings to dry for varying periods of time, at room temperature, and then subjecting them to the flame-propagation test at 180°. This test provides a measure of the time in which the coating remains a fire hazard. It is preferred that the coating be inflammable a short period of time after application.

The results of the two flammability tests are described in Tables III and IV.

TABLE III

Flammability of PVDF-based Skin Preparation Coating Materials

| Composition | Coating Wet/Dry | Flame Angle (°) | Specimen Consumed (%) | No. of Trials |
|---|---|---|---|---|
| Example 1 | Wet | 180 | 100 | 2 |
|  |  | 90 | 100 | 2 |
|  |  | 45 | 100 | 2 |
|  |  | 0 | 100 | 2 |
| Example 1 | Dry | 180 | 0 | 3 |
|  |  | 90 | 0 | 2 |
|  |  | 45 | 0 | 2 |
|  |  | 0 | 0 | 2 |

The results of the flame propagation test demonstrate that the PVDF-based coating will propagate a flame prior to drying, but quickly becomes inflammable. As shown in Table IV, the composition provides a surgical incision drape inflammable at the 180° test angle after a drying time of less than 15 seconds.

TABLE IV

Drying time required for surgical coating to become inflammable at 180° test angle

| Composition | Drying time (sec.) | No. of Trials |
|---|---|---|
| Example 1 | 8–13 | 5 |

TEST #2—FILM FLAMMABILITY WIHT HIGH ENERGY SURGICAL TOOLS

Films formed from the composition of this invention may be subjected to modern high energy surgical instruments, and must therefore be flame resistant. To determine the film's flame resistance, the composition described in EXAMPLE 2 was applied to the skin of an orange and the exterior skin portion of a ham hock, and allowed to dry for one minute. Following this dry time, commonly used surgical lasers (TABLE V) were employed to test their burn effect on the film coating. Neither laser resulted in burning or charring of the film coating. Dry films of the invention therefore do not pose a fire hazard when used in conjunction with the high energy devices present in modem surgical suites.

TABLE V

Flammability of PVDF-based coating used with High Energy Surgical Instruments

|  | Orange Flame | | Ham Hock Flame | |
|---|---|---|---|---|
| Instrument and Setting | yes | no | yes | no |
| Coherent VersaPlus Select Ng-Yag, Neodymium 1.06 μm laser: |  |  |  |  |
| Setting: High; Time: 120 seconds; Power: 60 watts |  | X |  | X |
| Coherent VersaPlus Select Nd-Yag, Holmium 2.1 μm laser: |  |  |  |  |
| Setting: High; Energy: 28 Joules; Rate: 20 pulses/second |  | X |  | X |
| ConMed Excalibur Plus Bovie: |  |  |  |  |
| Setting Standard; 50 coagulation |  | X |  | X |
| Setting Standard; 25 cut |  | X |  | X |
| Setting High; 120 coagulation |  | X |  | X |
| Setting High; 180 cut |  | X |  | X |
| Storz Fiber Optic: |  |  |  |  |
| 100% Illumination (max.); 1 minute |  | X |  | X |

TEST #3—MICROPOROSITY AND MOISTURE VAPOR TRANSMISSION RATE

Microporosity is an essential feature of a surgical incise drape. The moisture vapor transmission rate (hereinafter will be abbreviated as MTVR) is the measure of a films ability to allow air and water vapor to pass through while preventing the passage of liquid water. The MTVR is directly related to the microporous morphology of a film, and is defined by the presence of pores extending throughout the film. The MTVR provides a physical barrier to moisture while allowing moisture vapor to permeate through. The microporosity, and, thus the MTVR of the invention can be adjusted over a wide range of compositional variations. When examined under an electron microscope at 10,000×, a coating prepared form the composition in EXAMPLE I is found to contain pores of about 0.1 to 2.0 μm in diameter.

For the present test, several coating compositions were tested to determine the effect an amine-substituted acrylic monomer would have upon the formation of the microporous morphology required for a suitable surgical drape. It was found that the presence of the amine substituted acrylic monomer in combination with an aqueous acrylic emulsion (Rhoplex-R B-15J emulsion, Rohm and Haas Company, Philadelphia, Pa.), formed a film with the appropriate MTVR.

To test the MTVR of the present invention PVDF-based films having 0.5% w/w chlorhexidine acetate, PVDF-based films containing a combination of 0.5% w/w chlorhexidine acetate and 0.5% w/w silver sulfadiazine, PVDF-based films without antimicrobial, BLISTERFILM™ hydrocolloid wound dressing, and SARAN® food wrap were tested to determine which had the greatest MTVR (see FIG. 1). BLISTERFILM™ is a commercial hydrocolloid wound dressing that is described as having a relatively high MVTR that is adequate to promote wound healing.

The PVDF-based films were prepared following EXAMPLE 1 and EXAMPLE 2, respectively. Three replicates of each test sample were stretched over the mouths of 28.5 mm diameter tubes filled with 30 grams of distilled water. The tubes were clamped in an inverted position, and placed in a controlled environment room at 37° C. and 24% relative humidity for seven days. The amount of water loss due to evaporation was monitored over several days. The improved composition (EXAMPLE 1 and 2) demonstrated a relatively high moisture vapor transmission rate. As shown in FIG. 1, the percent of water lost over time remained linear up to 100% water loss. Furthermore, FIG. 1 illustrates the MTVR of the present invention is substantially greater than both the BLISTERFILM™ hydrocolloid wound dressing, and SARAN® food wrap. This result illustrates that a preferred feature of the invention is a substantially porous and breathable film. This preferred feature maintains the isothermic environment appropriate for a patient's body temperature, ensures adequate adhesion by preventing moisture buildup, and provides a route for the release of antimicrobial agents encapsulated within the coating.

TEST #4—EVALUATION OF INVENTION AS A PRIMARY IRRITANT

To determine whether the preferred composition of the invention causes skin irritation the following test was performed. One day prior to the application of the coating, the hair on the back of six New Zealand White rabbits was removed with clippers. The skin surface on one side of the shaved area was left untouched while the other side was irritated by scratching with a sharp object. A 0.5 nL portion of the PVDF-based coating from EXAMPLE 1 was applied to both the untouched and the irritated skin, and covered with one inch square pieces of gauze sponges. The application sites were further protected by wrapping the trunks of the animals with gauze, and securing with elastic bandage.

The untouched and irritated test sites were given a pre-assigned score for both erythema and edema formation 24 hours and 72 hours after application of the coating (TABLE VI). The sum of the eight erythema and edema values was divided by four to give a Primary Irritation score. The Mean Primary Irritation Index was determined by dividing the Primary Irritation score by six, the number of test animals. The coating reaction was then assigned a descriptive rating, from this Index, providing a Mean Primary Dermal Irritation score (TABLE VII).

TABLE VI

Evaluation of Skin Reations

| Erythema and Eschar Formation | Value |
|---|---|
| No Erythema | 0 |
| Very slight erythema (barely perceptible) | 1 |
| Well-defined erythema | 2 |
| Moderate to severe erythema | 3 |
| Severe erythema to slight eschar formation | 4 |

| Edema Formation | Value |
|---|---|
| No Edema | 0 |
| Very slight edema (barely perceptible) | 1 |
| Slight edema (edges of area well defined) | 2 |
| Moderate edema (raised about 1 mm) | 3 |
| Severe edema (raised more than 1 mm) | 4 |

TABLE VII

Mean Primary Irritation Index/Descriptive Rating

| Range of Values | Descriptive Rating |
|---|---|
| 0 | Non-Irritating |
| 0.1–1.9 | Mildly Irritating |
| 2.0–5.9 | Moderately Irritating |
| 6.0–8.0 | Severely Irritating |

Seven of the possible 48 test sites scored a one having only a barely visible erythema formation present (see Table VI). Thus, the composition of the invention had a Mean Primary Dermal Irritation score of 0.3. As shown in Table VII, mild irritants have values ranging from 0.1 to 1.9, indicating that the composition of the invention falls into the lowest end of the "mildly irritating" category. The slight irritation is expected with the introduction of a solvent to an area subjected to prior irritation. The results of this test demonstrate that the preferred composition of the invention does not cause any substantial skin irritation, but shows only mild signs of irritation when applied to previously irritated skin.

TEST #5—IN VIVO DURABILITY

A preferrable feature of a PVDF-based composition useful for a one-step skin-preparation and surgical drape is sufficient durability and adhesion under end-use conditions. To determine whether the invention provided the desired durability and adhesion, the coating was applied to the skin of human volunteers and subjected to end-use conditions.

The volunteers applied to the anti-cubital fossa of both the left and right arms the composition prepared in EXAMPLE I. The coatings were observed for eight hours or longer before the volunteer either showered or bathed. Each volunteer subjectively evaluated the results of the experiment according to a rating scale. The rating scale was the percentage of coating remaining intact at each examination.

The coatings remained 90% to 100% intact with no separation or detachment after bathing. After continuing to wear the coating for a total of 24 hours, no more than 10% of the film had lifted up along the edges of the coated area. The film was found to gradually detach and flake away after 48 hours of wear. The results of in vivo durability test demonstrate that the invention provides a substantially durable film coating resistant to body oils, perspiration, and hot water.

TEST #6—RESISTANCE OF THE COATING TO BIOLOGICAL FLUIDS

For use of the composition as a surgical drape it is highly desirable that the film remain substantially adherent and maintain adequate moisture vapor transmission in the presence of biological fluids. The PVDF-based coating prepared in EXAMPLE 1 was evaluated for its resistance to detachment in the presence of biological fluids by submersion of a film-coated microscope slide into blood, distilled water, saline, urine, and sodium heparin blood for three days at 37° C. The integrity of the coatings was rated daily according to a five-point scale, ranging from zero to four where zero represented 100% separation, and four represented no separation (0%) of the film from the slide. Following this protocol, the surgical drape coating remained fully adhered to the slide after three days continuous submersion in water, saline, and blood. In urine, slight lifting at the edges occurred after two days (rating of 3), which progressed to a rating of 2 (25–50% separation) after three days of continuous submersion.

To evaluate the films MTVR after exposure to biological fluids the test procedure described in TEST #3 was followed. The films compared were initially subjected to a 7 hour exposure to blood, urine, and water in a closed environment at 37° C., followed by a saline solution rinse. The films were then stretched over the mouths of 28.5 mm diameter tubes filled with saline solution to test the MTVR. After the 7 hour exposure, there was a small but non-significant decrease in the moisture vapor transmission rate, and no visible indications of leakage through the film.

The results of the resistance to biological fluids test demonstrate the integrity and continued protective function of the composition when used as a surgical drape or protective barrier for an incontinent individual.

TEST #7—DRUG DIFFUSION ASSAY

The ability of a film coating to release antimicrobial agents to the skin surface is a preferred embodiment of the present invention. To evaluate the ability of the present invention to deliver encapsulated antimicrobial agents to the skin surface, a zone of inhibition test was performed. For this test, the EXAMPLE 1 formulation containing either 0.5% chlorhexidine acetate, 0.5% chlorhexidine acetate and 0.5% silver sulfadiazine, or 2.0% silver sulfadiazine was analyzed. Two coatings of the improved formulation were applied on one side of a 9.8 mm polyethylene disc to an average thickness of 0.014 mm. Five discs were prepared for each test solution. Five disc coated with the improved composition without an encapsulated antimicrobial agent were included as controls.

Figure 2:
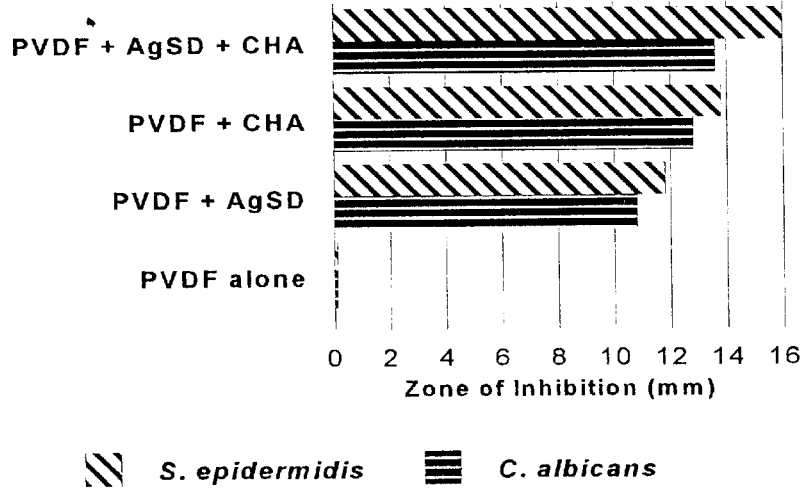
FIG. 2 illustrates a drug diffusion assay showing the ability of the coating of the present invention to release an antimicrobial agent for providing microbicidal activity against *S. epidermidis* (diagonal hatch) and *C. albicans* (horizontal hatch). The assay was performed with the present invention containing both chlorhexidine acetate (CHA) and silver sulfadiazine (AgSD), chlorhexidine alone, silver sulfadiazine alone, and with no antimicrobial agent present. The measure of microbicidal activity released by the coating of the present invention is plotted as the zone of inhibition in millimeters. The composition of the present invention with the highest microbicidal activity is characterized by a larger numerical value for the zone of inhibition. See Test #7 for details.

The coatings were allowed to completely dry and then inverted on buffered yeast morphology agar plates swabbed with an inoculum of *C. albicans* or *S. epidermidis*. This placed the film coating in direct contact with the inoculated yeast morphology agar plates. The plates were incubated at 37° C. for 24 hours. Determining the distance in millimeters from the periphery of the film coated disc to the sites of active microbial growth provides a measure of the zone of inhibition. The zone of inhibition is produced by diffusion out of the film of an encapsulated antimicrobial to the agar substrate, thereby eliminating any microbial growth that surrounds the film coated disc. Thus, the ability of a film to release increasing amounts of antimicrobial agent is characteristized by an expanded zone of inhibition. As shown in FIG. 2, the improved composition containing the 0.5% chlorhexidine acetate and 0.5% silver sulfadiazine combination provided the greatest zone of inhibition with a 16 mm zone of *S. epidermidis* inhibition. The results demonstrate that the improved PVDF-based coating can effectively release chlorhexidine acetate, silver sulfadiazine and a combination of chlorhexidine acetate and silver sulfadiazine. The control disc exhibited no inhibition and therefore no antimicrobial activity.

TEST #8—MICROBICIDAL ACTIVITY OF DRIED COATINGS

An effective surgical drape provides the desired microbicidal activity against a variety of microorganisms. To evaluate the microbicidal activity of the composition including an antimicrobial agent, a modified in vitro test found in the technical literature supplied by 3M Corporation for DURA-PREP™ was utilized. In the 3M study design, coatings were applied to filters pre-seeded with microorganisms followed by 5 minute homogenization of the filters. The homogenized filters were then plated on nutrient substrates. 3M's technical literature reports a 100% kill within 1 minute of application using this method. These results, however, are to be expected considering the 3M solution contains 74% isopropyl alcohol (w/w). Thus, the inventors were concerned that the improved compositions's high concentration of acetone, with its inherent microbicidal properties, would eliminate all viable microorganisms regardless of the encapsulated antimicrobial agent. The modified version of the in vitro test therefore involves coating the filter with the test composition, allowing the acetone to completely evaporate, and then seeding the filter with microorganisms.

The modified version provides a stringent test of the microbicidal properties of one of the desired compositions including an antimicrobial agent. The test was performed using the formulation prepared in EXAMPLE 1 containing by weight either 0.5% chlorhexidine acetate, or 0.5% chlorhexidine acetate and 0.5% silver sulfadiazine. The test for *Escherichia coli* was performed as follows:

1. *E. coli* was grown overnight on Trypticase Soy Agar (TSA) at 37° C.
2. The following morning, colonies of *E. coli* were swabbed from the plate and diluted to an O.D. 530 of 0.05 with phosphate buffered saline (PBS).
3. Gelman hydrophilic polypropylene membrane filters (47 mm, 0.045 μm) were placed on support and uniformly painted with the PVDF and antimicrobial combination using an artist brush. The polymer-coated membranes were allowed to air dry for 2 minutes at room temperature.
4. The bacterial suspension (0.1 ml) described above was placed on the coated membrane and aseptically spread uniformly across the film coated membrane.
5. At 0 minutes, 2 minutes, 10 minutes and 30 minutes the filters were aseptically place in 10 ml of Letheen +0.1% sodium thiosulfate to inactive the antimicrobial agent, and vortexed 30 seconds to dislodge the bacteria.
6. The suspension of dislodged bacteria was serially diluted in Phosphate buffered dilution water and plated on TSA plates for determination of the number of viable bacteria per ml.
7. Colonies were counted and recorded as the number of viable bacteria (per ml) dislodged from the surface of the PVDF-coated membranes. The log reduction in viability was determined by comparing the number of viable bacteria dislodged from the surface of the coating with and without an antimicrobial.

The results of the test show that the microbicidal activity of the dried PVDF-based composition containing a combination chlorhexidine acetate and silver sulfadiazine has substantial in vitro microbicidal activity. The test composition providing substantial reductions in colony forming units at 0, 2, 10 and 30 minute incubations.

The test was performed with similar results for *Staphylococcus epidermidis, Pseudomonas aeruginosa, Staphylococcus aureus, Proteus vulgaris, Candida albicans, Serratia marcesens*, and *Trichophyton mentagrophytes*. The results of the test demonstrate that antimicrobial agents encapsulated within the improved PVDF-based coating of the present invention provide substantial microbicidal activity in vitro against a variety organisms.

What is claimed is:

1. A film forming composition for providing a protective coating on a skin surface, comprising:
   (a) about 30 to 60% by weight of solids selected from the group consisting of polyvinylidene diflouride and the copolymers thereof;
   (b) about 10 to 20% by weight of solids of a polymer of monomers selected from the group consisting of a lower alkylacrylate, a lower alkyl (meth)acrylate, a hydroxy lower alkylacrylate, an alpha beta unsaturated carboxylic acid having an acid number of about 20 to 150, and the copolymers thereof;
   (c) about 30 to 60% by weight of solids of a polymer of monomers selected from the group consisting of a dialkylaminoalkyl (meth)acrylate and, a lower alkyl (meth)acrylate;
   (d) about 0.5 to 2.0% of water based on total composition weight;
   (e) an effective amount of an antimicrobial lipid; and
   (f) an aqueous organic solvent for dissolving all components.

2. A film forming composition for providing a protective coating on a skin surface, comprising:
   (a) about 30 to 60% by weight of solids selected from the group consisting of polyvinylidene diflouride and the copolymers thereof;
   (b) about 10 to 20% by weight of solids of a polymer of monomers selected from the group consisting of a lower alkylacrylate, a lower alkyl (meth)acrylate, a hydroxy lower alkylacrylate, an alpha beta unsaturated carboxylic acid having an acid number of about 20 to 150, and the copolymers thereof;
   (c) about 30 to 60% by weight of solids of a polymer of monomers selected from the group consisting of a dialkylaminoalkyl (meth)acrylate, and a lower alkyl (meth)acrylate;
   (d) about 0.5 to 2.0% of water based on total composition weight;
   (e) a lipid component being present in an amount of about 0.25 to 2.0 parts by weight per 10,000 parts by weight of polymer solids;
   (f) an effective amount of an antimicrobial agent; and
   (g) an aqueous organic solvent for dissolving all components.

3. The composition of claim 2, further comprising a medicament.

4. The composition of claim 3, wherein said medicament is selected from the group consisting of an anti-inflammatory agent, a steroid, an antiviral agent, an antifungal, an anticoagulant, an antiphlogisitic, a chemotherapeutic, a hemostatic, a cytostatic, and a hormone.

5. The composition of claim 4, wherein said cytostatic is a silver compound.

6. The composition of claim 2, wherein said antimicrobial agent is substantially releasable in an amount sufficient to substantially impart prolonged antimicrobial properties on said skin surface, said antimicrobial agent selected from the group consisting of antibiotics, iodophors, silver sulfadiazine, chlorhexadine and biologically active salts thereof.

7. The composition of claim 6, wherein said antibiotic is nystatin present in a quantity ranging from about 0.5 to 2.0% of the total weight of said film forming composition.

8. The composition of claim 2, wherein said solvent is selected from the group consisting of acetone, ethyl acetate, and mixtures thereof.

9. The composition of claim 2, wherein said solids comprise between about 5 to 10% of the total weight of said film forming composition.

10. The composition of claim 2, further comprising a dye soluble in said organic solvent.

11. The composition of claim 9, wherein said dye is Drug and Cosmetic Green No. 6.

12. The composition of claim 2, wherein said lipid component is selected from the group consisting of an unsaturated fatty acid, a saturated fatty acid, and a sphingolipid.

13. The composition of claim 2, wherein said lipid component is selected from the group consisting of ceramide Type III, ceramide Type IV, cholesterol, and linoleic acid.

14. The composition of claim 2, wherein said dialkylaminoalkyl methacrylate being about 6 to 16% of the total weight of all solids in the composition.

15. The composition of claim 2, wherein said dialkylaminoalkyl (meth)acrylate is selected from the group consisting of N,N-dimethylaminoethyl (meth)acrylate, N,N-diethylaminoethyl (meth)acrylate, t-butylaminoethyl (meth)acrylate and active salts thereof.

16. The composition of claim 2, wherein said protective coating having a moisture vapor transmission rate of about 0.1 to 1.0 $g/cm^2/day$, said moisture vapor transmission rate sufficient to substantially maintain the isothermic environment of said skin surface.

17. A method for eliminating and inhibiting microbial growth at a skin surface site, comprising the steps of:
    (a) applying to said skin surface site said film forming composition in claim 1;
    (b) allowing evaporation of solvent from said film forming composition to form a protective film coating;
    (c) allowing said protective coating to remain on said skin surface site for releasing antimicrobial agents in a quantity sufficient to substantially eliminate present microbes and inhibit microbial rebound growth on said skin surface site.

18. The method claimed in claim 17, wherein said site is a surgical procedure site and said film forming composition forms a substantially fluid resistant, substantially durable, substantially adherent surgical incise drape, said surgical incise drape capable of releasing a medicament, and an antimicrobial agent in a quantity capable of substantially imparting prolonged antimicrobial properties on said surgical procedure site.

19. The method claimed in claim 17, wherein said film forming composition is applied to the skin surface of an incontinent person forming a substantially fluid resistant barrier film capable of imparting prolonged antimicrobial properties on the skin surface of said incontinent person.

20. The method claimed in claim 17, wherein said applying is by painting, spreading, swapping, dipping or spraying.

21. The method claimed in claim 17, wherein said barrier film is about 0.010 mm to 0.015 mm thick, when dry, on the skin surface.

22. The composition of claim 1, wherein said composition when applied to a skin surface from said solvent dries in less than one minute forming a substantially durable, substantially fluid resistant, tack-free barrier film substantially adherent to said skin surface, said barrier film capable of releasing said antimicrobial agent in an amount effective to substantially impart prolonged antimicrobial properties on said skin surface, said barrier film being substantially porous, said pores ranging in dimension from about 0.1 microns to 2.0 microns in diameter.

23. The composition of claim 1 including an amine-substituted acrylic polymer in an amount to increase skin adhesion of said film.

* * * * *